US006620167B2

(12) United States Patent
Deslauriers et al.

(10) Patent No.: US 6,620,167 B2
(45) Date of Patent: Sep. 16, 2003

(54) ORTHOPEDIC SCREW HAVING DRIVER-LOCKING HEAD

(76) Inventors: Ricahrd J. Deslauriers, 87 Carmel Hill Rd., Woodbury, CT (US) 06798; Robert T. Potash, 20 Podunck Cir., South Windsor, CT (US) 06704; John R. Pepper, 224 Beacon Hill Dr., Cheshire, CT (US) 06410

( * ) Notice: Subject to any disclaimer, the term of this patent is extended or adjusted under 35 U.S.C. 154(b) by 195 days.

(21) Appl. No.: 09/978,119

(22) Filed: Oct. 17, 2001

(65) Prior Publication Data

US 2003/0074003 A1 Apr. 17, 2003

(51) Int. Cl.[7] .......................... A61B 17/56; F16B 23/00
(52) U.S. Cl. ................................ 606/73; 411/407
(58) Field of Search ........................ 606/72, 73, 104; 411/407, 402, 403, 406, 408; D8/397

(56) References Cited

U.S. PATENT DOCUMENTS

| 4,911,593 | A | * | 3/1990 | Kephart | 411/403 |
| 4,936,172 | A | * | 6/1990 | Jackson | 81/451 |
| 5,562,547 | A | * | 10/1996 | Borzone | 470/9 |
| 5,722,838 | A | * | 3/1998 | Czegledi | 411/407 |
| 6,261,291 | B1 | * | 7/2001 | Talaber et al. | 606/69 |
| 6,565,573 | B1 | * | 5/2003 | Ferrante et al. | 606/73 |

* cited by examiner

*Primary Examiner*—Eduardo C. Robert
*Assistant Examiner*—David C Comstock

(57) ABSTRACT

According to this invention an orthopedic screw having a first portion and a second portion is disclosed, wherein said first portion comprises a head having a substantially smooth exterior surface and further comprising a recessed portion, wherein said recessed portion comprises a polygonal shape and a deflection beam, such that said first portion receives a driver head within said recessed potion, and wherein said second portion comprises an elongated portion adapted for insertion into a substrate.

15 Claims, 3 Drawing Sheets

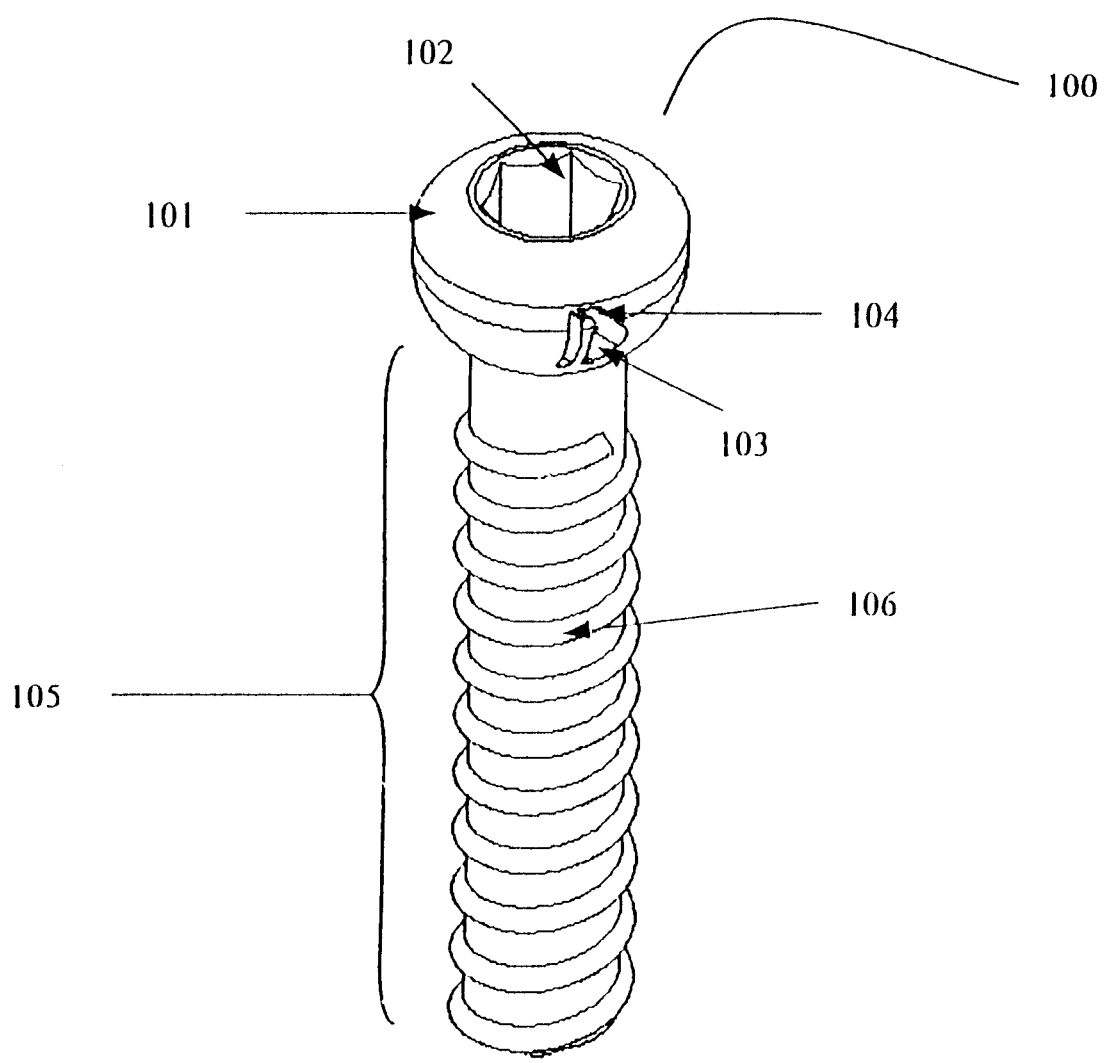

ORTHOPEDIC SCREW HAVING DRIVER-LOCKING HEAD

BACKGROUND OF THE INVENTION

1. Field of the Invention

This invention relates to the field of surgical screws, and in particular screws for use in orthopedic surgical procedures.

2. Description of the Related Art

The related art of the field teaches a number of different types of surgical screws that may be used in a human body for insertion into a substrate, such that said screws are inserted into bones, and whereby tissue or muscle may then cover the head of the screw. Certain inventions disclose surgical screws, and which screws may employ standard driver insertions points that may consist of cruciform recesses, slot recesses, or polygonal recesses. However, a shortcoming of these devices is that they may not lock, or mechanically retain, themselves to a driver head, and thus may have a tendency to fall off the driver head. This shortcoming may result in increased difficulty in their application and further may increase the amount of time required to fasten these screws to a substrate. Another shortcoming of these devices is that they may be designed and manufactured such that the head portion of these screws may have a rough or angular outer surfaces, and which angularity may cause increased irritation of tissue and muscles covering the head of the screw after their application.

Furthermore, there are other teachings that may demonstrate a self-retaining screw to a driver head, however, these devices may also be designed and manufactured such that the screw head may have an outer surface that may be angular or irregularly shaped. Such self-retaining screws may consist of a tapered recess, wings, or twisted hexagonal recesses. A shortcoming of these devices may be that they are weak in structure and may also have a tendency not to tightly secure a driver head, whereby these screws may have a tendency to disengage themselves from the driver head. Furthermore, these devices may be subject to yet another shortcoming that upon insertion to a substrate, the head of these screws may be covered with tissue and/or muscle such that the angular or irregularity may cause increased discomfort and added irritation to the tissue and/or muscle at the insertion site. Additionally, these devices may have a retaining fixture that may not provide strength for a load such that the retaining fixture may be caused to break from the load force required for its insertion into a substrate.

BRIEF SUMMARY OF THE INVENTION

Therefore a need has arisen for an orthopedic screw that overcomes these and other shortcomings of the related art. A technical advantage of the present invention is to provide an orthopedic screw wherein tissue irritation may be substantially reduced and minimized. Another technical advantage of the present invention is to provide an orthopedic screw that may be mechanically retained to a driver head. Still yet another technical advantage of the present invention is to provide an orthopedic screw that may provide for a load-bearing surface having a retaining mechanism located on the same plain, and such that the retaining mechanism will not fail under the necessary load force for insertion into a substrate.

According to an exemplary embodiment of the present invention a self-retaining orthopedic screw is described. The present invention may have a first portion and a second portion, wherein said first portion may comprise a head portion having substantially smooth outer surface and may further comprising a recessed portion on a top surface of said head portion, wherein said recessed portion may comprise a deflection beam having at least one protrusion extending into said recessed portion, wherein said deflection beam may be substantially enclosed within said recessed portion, and wherein said second portion may comprise an elongated portion having a threading such insertion into a substrate is facilitated.

Other objects, features, and advantages will be apparent to persons of ordinary skill in the art in view of the following detailed description of the invention and the accompanying drawings.

BRIEF DESCRIPTION OF THE SEVERAL VIEWS

FIG. 1 depicts a self-retaining surgical screw according to the preferred embodiments of the present invention.

DETAILED DESCRIPTION OF THE INVENTION

Figure 2A:
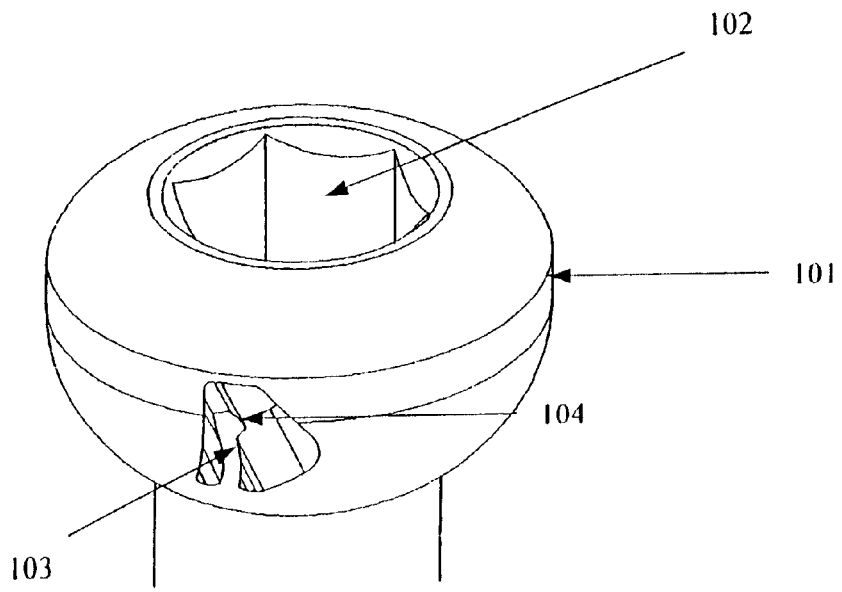
FIG. 2a depicts the head portion of the surgical screw according to the preferred embodiments of the present invention.

Preferred embodiments of the present invention and their advantages may be understood by referring to FIGS. 1–3b, like numerals being used for like corresponding parts in the various drawings.

FIG. 1 shows an orthopedic screw 100 according to the preferred embodiments of the present invention. Screw 100 may have a first portion and a second portion, wherein said first portion may comprise head portion 101 having a substantially smooth exterior surface and further comprising a recessed portion 102, wherein said recessed portion comprises a polygonal shape and a deflection beam 103, and wherein second portion 105 may comprise an elongated member adapted for insertion into a substrate.

In its preferred embodiments, screw 100 may be manufactured from a material selected from one of the group consisting of titanium, titanium alloy, stainless steel, cobalt chromium, medical-grade surgical steel. In other embodiments, screw 100 may be manufactured from a synthetic bone material or a biocompatible material. Furthermore, according to other embodiments of the present invention screw 100 may be manufactured with a composite of an antibacterial agent and a biocompatible material, or alternatively, screw 100 may be coated with an antibacterial agent.

The first portion of Screw 100 may be comprised of a head portion 101 having substantially smooth outer surface and a recessed portion 102 on a top surface of said head portion 101, wherein said recessed portion 102 may comprises a deflection beam 103 having at least one protrusion 104 that may extending into said recessed portion 102, wherein said deflection beam 103 is substantially enclosed within said recessed portion 102.

Screw 100 further may be comprised of a second portion 105 that may comprise an elongated portion that may have threading 106 such that insertion into a substrate is facilitated. FIG. 1a depicts other embodiments of second portion 105, wherein threading 106 permits self-tapping of screw 100 into a substrate, such that tapping of the substrate may be eliminated.

Figure 2B:
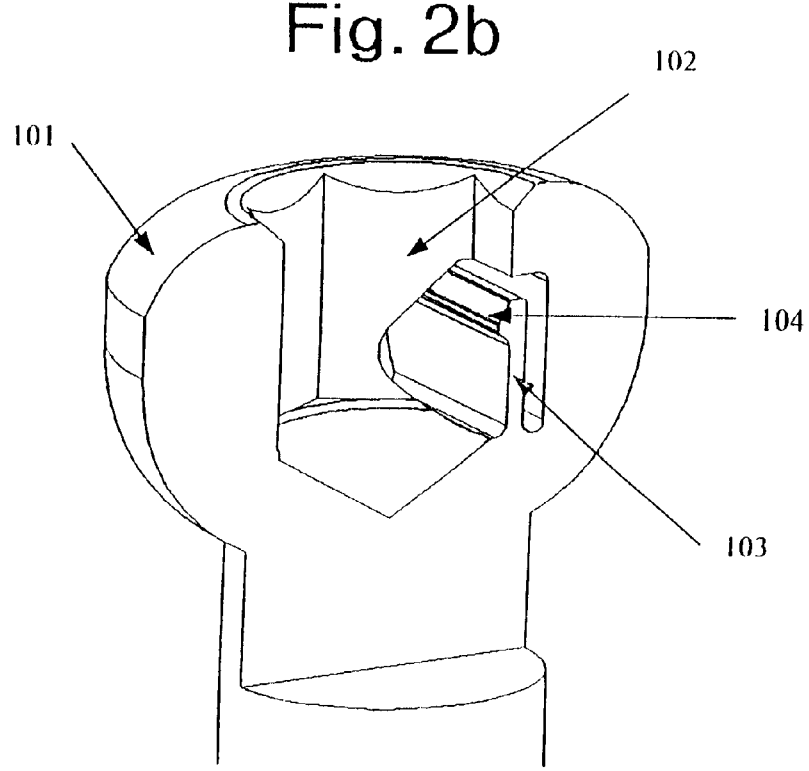
FIG. 2b depicts a cut-away view of the head portion of the surgical screw according to the preferred embodiments of the present invention.

FIGS. 2a–2b show recessed portion 102 according to the preferred embodiments. Wherein recessed portion 102 may have a first shape, wherein said first shape may be polygonal. The polygonal shape of recessed portion may provide for adequate load bearing support, such that recesses portion 102 may not become stripped during insertion into a substrate and rendering screw 100 useless, and such that deflection beam 103 may be protected from excessive loads causing deflection beam 103 to break during the insertion process. According to an exemplary embodiment of recessed portion 102, said first shape may be hexagonal. In other embodiments of recessed portion 102, said first shape may be four sided, such as a square or a rectangle.

Figure 3A:
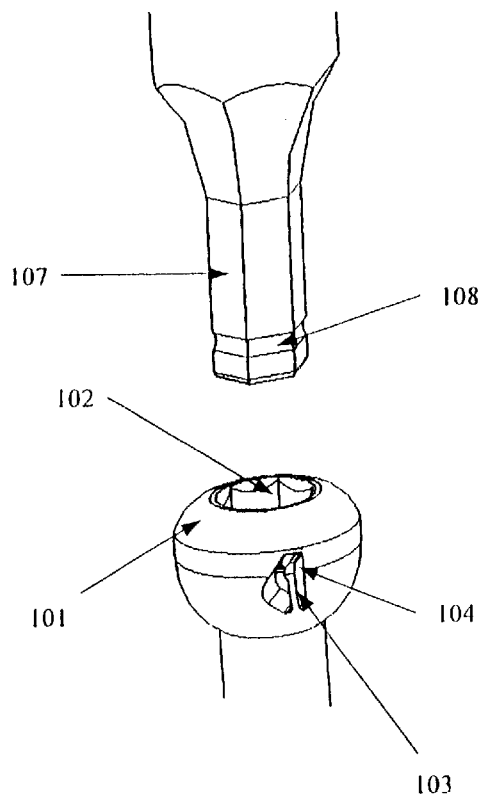
FIG. 3a depicts the surgical screw in connection with the head portion of a driver according to the preferred embodiments of the present invention.
Figure 3B:
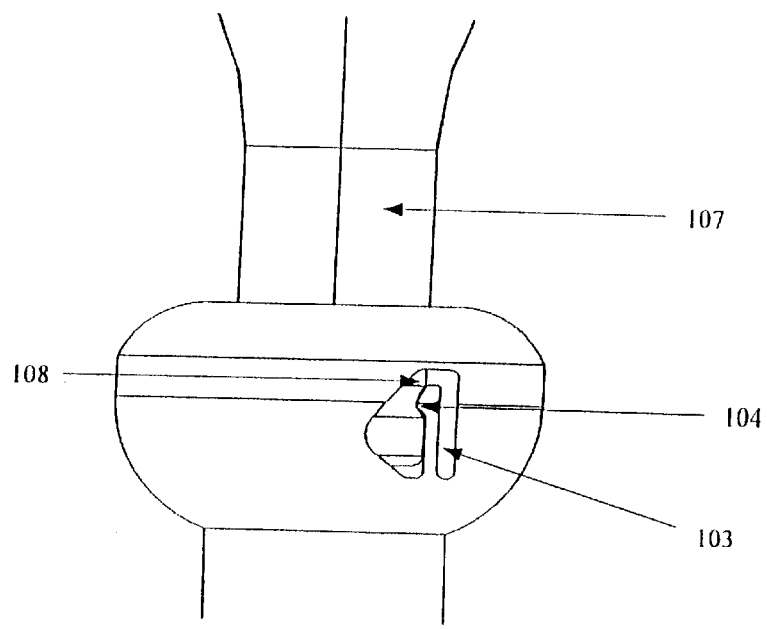
FIG. 3b depicts the surgical screw and a driver head according to the preferred embodiments of the present invention.

FIGS. 3a–3b depict screw 100 in connection with driver head 107 in accordance with a preferred method of use. In its preferred embodiments, recessed portion 102 interconnects with a driver head 107, wherein driver head 107 may have a second shape, wherein said second shape is polygonal, and wherein said first shape and said second shape may be substantially the same, such that a secure and tight fit may be caused between driver head 107 and recessed portion 102. In its preferred embodiments, driver head 107 may further be comprised of a locking groove 108, such that upon insertion of driver head 107 into recessed portion 102, then deflection beam 103 may be caused to flex and then to return to non-deflected position upon protrusion 104 meeting with locking groove 108, such that head portion 101 may be securely fastened to driver head 107 through the application of radial energy provided from deflection beam 103.

Other embodiments of screw 100 (not shown) may provide for recessed portion 102 that may interconnect with a driver head, wherein said driver head may be substantially uniform, such that said driver head may not comprise a locking groove, then upon insertion of said driver head into said recessed portion said deflection beam 103 is caused to flex such that said head portion 101 may be secured to said driver head through the application of friction being applied from the connectivity of said protrusion 104 and the application of radial force from protrusion 104 to said driver head.

While the invention has been described in connection with preferred embodiments, it will be understood by those of ordinary skill in the art that other variations and modifications of the preferred embodiments described above may be made without departing from the scope of the invention. Other embodiments will be apparent to those of ordinary skill in art from a consideration of the specification or practice of the invention disclosed herein.

What is claimed is:

1. A orthopedic screw having a first portion and a second portion;

said first portion comprising a head portion having substantially smooth outer surface and further comprising a recessed portion on a top surface of said head portion, wherein said recessed portion comprises a deflection beam having at least one protrusion extending into said recessed portion, wherein said deflection beam is substantially enclosed within said recessed portion, and wherein said second portion comprises an elongated portion having a threading.

2. The device of claim 1, wherein said recessed portion is a polygonal shape.

3. The device of claim 2, wherein said polygon is a hexagon.

4. The device of claim 2, wherein said polygon is a square.

5. The device of claim 2, wherein said polygon is a pentagon.

6. The device of claim 2, wherein said polygon is an octagon.

7. The device of claim 1, wherein said screw is manufactured from a material selected from one of the group consisting of titanium, titanium alloy, stainless steel, cobalt chromium, medical grade surgical steel.

8. The device of claim 1, wherein said locking screw is manufactured from a synthetic bone material.

9. The device of claim 1, wherein said locking screw is manufactured from a biocompatible material.

10. The device of claim 1, wherein said locking screw is manufactured with a composite of an antibacterial agent and a biocompatible material.

11. The device of claim 1, wherein said locking screw is coated with an antibacterial agent.

12. The device of claim 1, wherein said second portion comprises a self-tapping threading.

13. A method of using the device of claim 1, wherein said recessed portion having a first shape interconnects with a driver head having second shape and a locking groove, wherein said first shape and said second shape are substantially the same, which method comprises inserting said driver head into said recessed portion said deflection beam is caused to flex and then return to a non-deflected position upon said protrusion meeting with said locking groove such that said head portion is secured to said driver head, wherein said screw is then inserted into a substrate, and then wherein said driver head is removed from said recessed portion.

14. A method of using the device of claim 1, wherein said recessed portion having a first shape interconnects with a driver head having second shape, wherein said first shape and said second shape are substantially the same, which method comprises inserting said driver head into said recessed portion, wherein said deflection beam is caused to flex and secure said driver head through the application of radial friction energy being applied from the connectivity of said protrusion of said deflection beam to said driver head.

15. A screw comprising a first portion and a second portion, wherein said first portion comprises a head having a substantially smooth exterior surface and further comprising a recessed portion, wherein said recessed portion comprises a polygonal shape and a deflection beam, wherein said recessed portion is adapted to engage a driver head within said recessed portion, and wherein said second portion comprises an elongated member adapted for insertion into a material.

* * * * *